United States Patent
Briand et al.

(10) Patent No.: US 7,892,311 B2
(45) Date of Patent: Feb. 22, 2011

(54) USE OF ULVANS AS ELICITORS OF MECHANISMS FOR NITROGEN ABSORPTION AND PROTEIN SYNTHESIS

(75) Inventors: Xavier Briand, Lezardrieux (FR); Stéphanie Cluzet, Toulouse (FR); Bernard Dumas, Montrabe (FR); Marie-Thérése Esquerre-Tugaye, Castanet-Tolosan (FR); Sylvie Salamagne, Gressy En France (FR)

(73) Assignee: Timac Agro International, Saint Malo (FR)

( * ) Notice: Subject to any disclaimer, the term of this patent is extended or adjusted under 35 U.S.C. 154(b) by 607 days.

(21) Appl. No.: 10/594,609

(22) PCT Filed: Mar. 30, 2005

(86) PCT No.: PCT/FR2005/000764

§ 371 (c)(1),
(2), (4) Date: Jul. 2, 2007

(87) PCT Pub. No.: WO2005/094581

PCT Pub. Date: Oct. 13, 2005

(65) Prior Publication Data

US 2008/0127695 A1    Jun. 5, 2008

(30) Foreign Application Priority Data

Mar. 30, 2004   (FR)   .................. 04 03267

(51) Int. Cl.
    *C05F 11/00*   (2006.01)
    *C09K 17/40*   (2006.01)
    *C09K 17/14*   (2006.01)
    *C05F 11/10*   (2006.01)

(52) U.S. Cl. .................. 71/23; 47/58.1 SC; 71/11; 71/28; 71/29; 71/30; 71/33; 71/32; 71/34; 71/58; 71/59; 71/60; 71/63; 71/903; 504/100; 504/113

(58) Field of Classification Search .............. 71/11, 71/23, 28, 29, 30, 33, 34, 32, 58, 59, 60, 71/63, 903; 47/58.1 SC; 504/100, 113
See application file for complete search history.

(56) References Cited

U.S. PATENT DOCUMENTS 5,508,033 A * 4/1996 Briand .................. 424/195.17
5,672,503 A * 9/1997 Nairn et al. .................. 435/422
2007/0232494 A1 * 10/2007 Briand et al. ............... 504/189

FOREIGN PATENT DOCUMENTS

EP    1 437 334    7/2004

OTHER PUBLICATIONS

OligoTech(R), Product Catalouge, Elicityl, Jun. 2009, p. # 36.*
Whitehead et al. "Differential patterns of phytoalexin accumulation and enzyme induction in wounded and elicitor-treated tissues of *Phaseolus vulgaris*", 1982, Planta Springer-Velag, vol. 1554, 156-164.*
International Search Report for International Application No. PCT/FR2005/000764 dated Aug. 16, 2005.
Bi et al., "Studies of Aqueous Extracts of Three Green Algae as an Elicitor of Plant Defence Mechanism" *Pak. J. Bot..* vol. 13, No. 1 pp. 193-198 (1999).
Ray et al. "Cell-Wall Polysaccharides From the Marine Green Alga *Ulva "Rigida"* (Ulvales, Chlorophyta). Extraction and Chemical Composition" *Carbohydrate Research*. vol. 274 pp. 251-261 (1995).
Ray et al. "Cell-Wall Polysaccharides From the Marine Green Alga *Ulva "Rigida"*(Ulvales, Chlorophyta). Chemical Structure of Ulvan" *Carbohydrate Research* vol. 274 pp. 313-318 (1995).
Lahaye et al. "Cell-Wall Polysaccharides From the Marine Green Alga *Ulva "Rigida"* (Ulvales, Chlorophyta) NMR Analysis of Ulvan Oligosaccharides" *Carbohydrate Research* vol. 283 pp. 161-173.
Quemener et al. "Sugar Determination in Ulvans by a Chemical-Enzymatic Method Coupled to High Performance Anion Exchange Chromatography " *Journal of Applied Phycology* vol.9 pp. 179-188.
Lopez-Mosquera et al. "Effects of Seaweed on Potato Yields and Soil Chemistry" Database accession No. PREV199799753675 and "Biological Agriculture and Horticulture" vol. 14 No. 3 pp. 199-205 (1997).

* cited by examiner

*Primary Examiner*—Wayne Langel
*Assistant Examiner*—Syed Iqbal
(74) *Attorney, Agent, or Firm*—Hamre, Schumann, Mueller & Larson, P.C.

(57) ABSTRACT

The present invention relates to the use of ulvans, in particular extracted from green algae of the genus *Ulva* or *Enteromorpha*, or of ulvan-derived oligosaccharides, as elicitors of mechanisms for nitrogen absorption and protein synthesis.

It also relates to a fertilizing product containing ulvans and to the use thereof in a plant treatment method.

21 Claims, No Drawings

USE OF ULVANS AS ELICITORS OF MECHANISMS FOR NITROGEN ABSORPTION AND PROTEIN SYNTHESIS

The present invention, which can be used in the agricultural field, essentially relates to the use of ulvans, in particular extracted from green algae of the genus *Ulva* or *Enteromorpha*, or of ulvan-derived oligosaccharides, as elicitors of mechanisms for nitrogen absorption and protein synthesis.

The present invention also relates to fertilizing compositions, such as, for example fertilizers containing these ulvans or ulvan-derived oligosaccharides and also to a method for treating plants or soils using them.

In the context of the present description, the expression "fertilizing composition" is intended to denote any product whose use is intended to ensure or improve the physical, chemical or biological properties of soils and also the nutrition of plants.

Such a composition may, for example, be a fertilizer applied via the roots or via the leaves.

It is known that fertilizers are defined as fertilizing substances whose main function is to provide plants with elements that can be directly used for their nutrition (major fertilizing elements, secondary fertilizing elements and trace elements).

To this effect, root or leaf fertilizers generally use sources of nitrogen, of phosphorus and of potassium and also trace elements and amino acids.

Plants absorb mainly nitrogen, which is a nutritive element essential to their growth.

The nitrogen is generally provided in the form of nitrate or ammonium, the use of which in large amounts poses problems from an ecological point of view.

One of the possible responses to the undesirable effects of fertilization with nitrates consists in improving the efficiency of absorption of nitrogen and of assimilation thereof, i.e. the incorporation thereof into organic molecules, and in particular into proteins.

In order to be absorbed by the plant, mineral nitrogen must cross the cell walls and membranes. The crossing of the membrane, which surrounds the cell, constitutes the determining step in the plant's control of its mineral nutrition.

At this stage, the mechanisms of entry of nitrogen into the plant are controlled by transporters.

Subsequently, the ammonium derived from the reduction of the nitrate or absorbed directly by the roots or the leaves is integrated into organic molecules so as to give glutamine and glutamate. These two reactions are catalyzed by glutamine synthase and glutamate synthetase. These enzymes can be considered, under certain conditions, to be limiting factors for nitrogen assimilation.

Ammonium therefore appears to be an essential intermediate of the plant's nitrogen metabolism.

This nitrogen is then transferred to other molecules so as to form amino acids. The carbon-based material constituting amino acids and the energy required for these reactions to be carried out are provided by photosynthesis and respiration.

The amino acid synthesis takes place mainly in the chloroplasts. The assimilation of $CO_2$ provides the carbon-based backbone required for amino acid synthesis.

At this level, various enzymes such as enolase, citrate synthase and also isocitrate dehydrogenase play a key role in the production of the amino acid precursors obtained from the conversion of the 3-phosphoglycerate produced during photosynthesis.

Triosephosphate isomerase is responsible for the step for conversion of glyceraldehyde phosphate to dihydroacetone phosphate. The dihydroacetone phosphate exported from the chloroplast represents not only an important precursor for the synthesis of sugars, but also a transport metabolite for energy and reducing equivalents. Dihydroacetone phosphate is available for syntheses (sucrose, proteosynthesis) or becomes converted to 3-phospho-D-glycerate, transferring its energy to ADP and its hydrogen to NAD+, which are required for cell metabolism, and in particular for the synthesis of glutamine and glutamate.

Peroxidases are, for their part, known for their involvement in growth, via their activity on cell division. The enzymes glutathione peroxidase and superoxide dismutase thus make it possible to maintain a high photosynthetic activity by providing an effective detoxification of the free radicals produced during this process.

It is known that the synthesis or the activity of the transporters and of the various enzymes involved in these mechanisms can vary in response to a certain number of signals, regardless of whether the latter are external (light, nitrogen supply, chemical substances, etc.) or internal (circadian rhythm). Thus, in order to increase the capacity for response to nitrogenous fertilization in terms of absorption of mineral nitrogen, of growth and of protein production by a plant, one of the possible strategies consists in simulating, beforehand, the reactions linked to nitrogen metabolism and carbon metabolism through the use of signal molecules.

Marine algae constitute an abundant plant resource and have, for a long time, been used in coastal regions as soil fertilizers. Seed germination, the production of better yields, resistance to diseases, and a longer storage period for fruit have been demonstrated following treatment of several plants with algal extracts. The conclusions in terms of plant health and growth had essentially been attributed to the richness in betains, plant hormones and trace elements of the algae used.

It is in this context that it has been discovered, and this constitutes the basis of the present invention, that ulvans, in particular extracted from green algae, and the oligosaccharides derived from the latter make it possible, entirely surprisingly and unexpectedly, to stimulate the expression of the genes of nitrogen metabolism (ammonium transporter, nitrite reductase, glutamate synthase and glutamine synthetase) and also certain genes of carbon metabolism, in particular involved in the provision of carbon-based material required for amino acid synthesis. This high metabolic activity is supported by a stimulation of cell division processes (peroxidases) and an effective detoxifying activity required for controlling the overproduction of free radicals generated by a high photosynthetic activity.

These ulvans can therefore be used as a supplement in fertilizing compositions, such as fertilizers, as activators of the absorption of mineral nitrogen and of the assimilation thereof in the form of proteins.

Such compositions allow an increased organic nitrogen production corresponding to the growth needs of the crop, which will be expressed in particular in terms of an enhanced yield. These compositions also make it possible to increase the protein content and the nutritional value of protein-yielding plants and forages.

These compositions also make it possible to reduce the risks of toxicity caused by an excessive accumulation of ammonium ions in the leaves or to reduce nitrate accumulations in the leaves.

Thus, according to a first aspect, the present application aims to cover the use of ulvans, in particular extracted from green algae of the genus *Ulva* or *Enteromorpha*, or of ulvan-derived oligosaccharides, as elicitors of mechanisms for nitrogen absorption and protein synthesis.

The ulvans which can be used according to the invention are water-soluble polysaccharides present in particular in the cell walls of green algae of the genera *Ulva* and *Enteromorpha*.

The ulvans are defined more specifically as highly sulfated acidic polysaccharides and are essentially composed of units derived from rhamnose 3-sulfate, from xylose, from xylose 2-sulfate, from glucuronic acid and from iduronic acid.

The following four repeating units are in particular characteristic of ulvans:

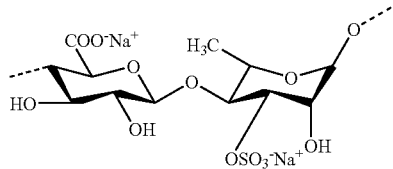

>4)-β-D-GlcA-(1>4)-α-L-Rha 3 sulfate (1>

(also called ulvanobiouronic acid 3-sulfate type A)

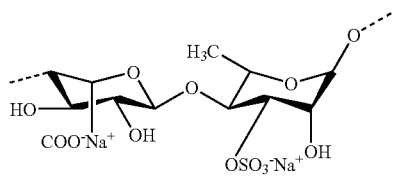

>4)-α-L-IdoA-(1>4)-α-L-Rha 3 sulfate (1>

(also called ulvanobiuronic acid 3-sulfate type B)

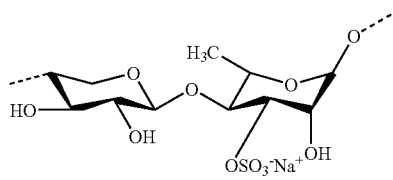

>4)-β-D-Xyl-(1>4)-α-L-Rha 3 sulfate (1>

(also called ulvanobiose acid 3-sulfate)

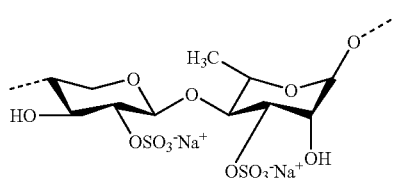

>4)-β-D-Xyl 2-sulfate-(1>4)-α-L-Rha 3 sulfate (1>

(also called ulvanobiose acid 2',3-disulfate)

Ulvans represent between 5 and 20% of the dry weight of the alga. Their molecular weight ranges between 90 000 and 500 000 g·mol$^{-1}$ in the genera *Ulva* and *Enteromorpha*.

Advantageously, the ulvans used according to the present invention are extracted from algae chosen from the group consisting of the following species: *Ulva armoricana, Ulva rigida, Ulva rotundata, Ulva lactuca, Enteromorpha intestinalis* and *Enteromorpha compressa*.

Extracts of algae rich in ulvans which can be used in the context of the present invention can be obtained from the abovementioned algae species, by means of a method generally comprising the following steps: washing, milling, extraction (solid-liquid separation) and, optionally, fractionation and concentration.

The extract obtained can be more or less concentrated according to the use envisioned. Complete dehydration of this extract, allowing it to be provided in a water-soluble pulverulent form, can be obtained, for example, by drying in a drum or by spraying.

The ulvan-derived oligosaccharides which can be used in the context of the invention can be obtained by acid hydrolysis or enzymatic hydrolysis using the abovementioned extracts.

The extraction conditions and the nature of the algae will be chosen such that the extract obtained has the concentration desired in the application envisioned. These choices may be readily made by those skilled in the art, in particular by taking into account the general indications which will follow.

In general, the amount of ulvans or of ulvan-derived oligosaccharides given to the plants is from 0.1 g to 100 g per liter, and preferably of the order of 1 g per liter, when applied in liquid form via the leaves or in nutritive solutions for the roots (hydroponics, dropwise, etc.) or else from 10 to 1000 g/ha, and preferably of the order of 200 g/ha, when applied in solid form in pulverulent or granulated fertilizers.

The amount of ulvans given to the plants must be sufficient to stimulate the expression of the genes involved in the elicitation of mechanisms for nitrogen absorption and protein synthesis. This amount is variable according to the nature of the plant to be treated and the method of treatment (administration via the leaves or via the roots). This amount may in particular be determined case by case by carrying out macroarray tests as defined below.

According to a second aspect, the present application aims to protect a plant or soil treatment method intended to activate elicitation reactions of mechanisms for nitrogen absorption and protein synthesis, characterized in that it comprises the application, to said plants or soils, of an effective amount of ulvans, in particular extracted from green algae of the genus *Ulva* or *Enteromorpha*, or of ulvan-derived oligosaccharides.

Advantageously, the application to the plants will be carried out via the leaves or via the roots.

The effective amount of ulvans or of ulvan-derived oligosaccharides given to the plants is from 0.1 g to 100 g per liter, and preferably of the order of 1 g per liter, when applied in liquid form via the leaves or in nutritive solutions for the roots (hydroponics, dropwise, etc.), or else from 10 to 1000 g/ha, and preferably of the order of 200 g/ha, when applied in solid form in pulverulent or granulated fertilizers.

By way of examples of fertilizing products in accordance with the invention, mention will be made of calcareous enriching agents, organic enriching agents and crop supports, root fertilizers of the type NP, PK, NPK, etc., leaf fertilizers or nutritive solutions for the roots.

The fertilizing substances which can be used in combination with the ulvans or the ulvan-derived oligosaccharides may be varied in nature and may be chosen, for example, from urea, ammonium sulfate, ammonium nitrate, natural phosphate, potassium chloride, ammonium sulfate, magnesium nitrate, manganese nitrate, zinc nitrate, copper nitrate, phosphoric acid and boric acid.

The present invention can also be used in the treatment of a very large variety of plants.

Among the latter, mention will be in particular be made of: large crop plants such as cereals (wheat, maize),
protein-yielding plants (pea),
oil-yielding plants (soybean, sunflower),
prairial plants used for animal feed,
specialized crops such as, in particular, crops for market gardening (lettuce, spinach, tomato, melon), grapevine, tree cultivation (pear, apple, nectarine), or horticulture (rose bushes).

The expression "plant" is intended to denote, in the present application, the plant considered as a whole, including its root system, its vegetative system, the grains, seeds and fruits.

The present invention will now be illustrated by means of the following nonlimiting examples.

In these examples, and unless otherwise indicated, the percentages are expressed by weight and the temperature is ambient temperature.

EXAMPLE 1

Method for Preparing an Ulvan-Rich Alga Extract which can be Used in the Context of the Invention A—General Description a) Preparation of Ulvans The ulvan fraction is obtained by aqueous extraction of fresh algae (100 g of fresh algae per liter of water).

The extraction is carried out with stirring at 90° C. for 2 hours. The extract is then filtered through a membrane (80 μm porosity). The solvent (water) is evaporated off so as to obtain a water-soluble powder.

b) Preparation of Oligoulvans

The ulvans prepared as indicated in a) above are hydrolyzed in 1 liter of acid solution (trichloroacetic acid or hydrochloric acid concentrated at 2-3 mol $L^{-1}$) at 100° C. for 30 min to 1 h, preferably of the order of 40 min.

Glucuronic acid, aldobiuronic acid, ulvanobiouronate and iduronic acid were identified in the hydrolysis products.

B. Detailed Example of Extraction:

An extract of *Ulva armoricana* enriched in ulvans, and in particular in derivatives of iduronic acid of xyloidurorhamnan type, was obtained according to the following experimental protocol:

a) Washing

Fresh algae of *Ulva armoricana* type are subjected to two successive washes in a tank of water, in order to remove the sand and gravel.

The algae are then placed in stainless steel wire mesh baskets before being introduced into tanks where they are covered with water.

Agitation by means of aeration nozzles makes it possible to maintain the algae in suspension, thus promoting the settling out of impurities.

b) Milling

The algae, thus washed, are drained and then milled into pieces of 1 to 10 mm.

c) Extraction 1000 kg of algae are dispersed in a heating reactor containing 10 000 kg of an aqueous solution brought to a temperature of 90° C. The whole is kept at this temperature for a period of approximately 2 hours.

Prior to the extraction, the algal cells already milled are micro-ruptured by means of an ULTRA-TURAX® homogenizer in order to promote extraction. The separating process occurs after 2 hours of extraction.

d) Separation

The soluble fraction rich in iduronic acid derivatives of xyloidurorhamnan type is separated from the algal debris by centrifugation (solid-liquid separation).

The centrifuged extract is then filtered, either through a diatomaceous earth filter, or through a plate filter, and then again filtered through a membrane of up to 1 μm.

The filtrate thus obtained contains between 0.1 and 1% by weight of dry extract.

The extract thus prepared can be used in a more or less concentrated form, the final concentration being determined according to the desired content of derivatives that are active in the application envisioned.

Thus, the filtrate mentioned above can be concentrated, for example by means of a falling-film evaporator, such that the dry extract represents from 10 to 60% by weight of said filtrate.

Complete dehydration can also be obtained, for example, with a drum dryer or by spraying, when a presentation in water-soluble pulverulent form is desired.

By proceeding as described above, various extracts were prepared from six species of green algae of the genus *Ulva* or *Enteromorpha*. The composition of these dry extracts is given in Tables 1A and 1B below.

TABLE 1A

Composition of the extracts of green algae

| Alga | % of ulvans (% of the dry weight of the alga) | % of total sugars | % of sulfates | % of proteins |
|---|---|---|---|---|
| Ulva armoricana | 7-15 | 50-80 | 10-20 | 3-7 |
| Ulva rigida | 5-18 | 50-80 | 13-17 | 1-10 |
| Ulva rotundata | 6-15 | 50-70 | 10-20 | 1-10 |
| Ulva lactuca | 5-17 | 50-70 | 10-20 | 1-8 |
| Enteromorpha intestinalis | 5-15 | 45-75 | 15-20 | 1-10 |
| Enteromorpha compressa | 5-16 | 50-75 | 10-20 | 1-12 |

TABLE 1B

Monosaccharide and uronic acid composition of the extracts of green algae

| Alga | Rha | Gal | Glc | Xyl | GlcA | IdoA |
|---|---|---|---|---|---|---|
| Ulva armoricana | 45-50 | 1-4 | 5-20 | 6-15 | 15-25 | 5-15 |
| Ulva rigida | 50-60 | 0.5-2 | 5-8 | 5-15 | 18-35 | 2-5 |
| Ulva rotundata | 45-55 | 1-3 | 5-15 | 5-25 | 16-30 | 0.5-5 |
| Ulva lactuca | 45-60 | 0.5-5 | 2-6 | 1-10 | 15-25 | 2-5 |
| Enteromorpha compressa | 25-50 | 1-5 | 2-10 | 5-15 | 10-20 | 5-10 |
| Enteromorpha intestinalis | 30-50 | 1-4 | 1-5 | 6-15 | 15-20 | 5-10 |

EXAMPLE 2

A—Effects of the Ulvans on the Expression of the Genes of a Model Plant

An overall analysis of the expression of numerous genes involved in the defense of a model plant was carried out using functional genomic techniques. The leguminous plant *Medicago truncatula* (large number of available DNA sequences) was used as model plant.

The effect of the ulvans was thus studied on more than 25 genes involved in the nitrogen and carbon metabolism, and in oxidative processes linked to cell division in this model plant, by macroarray analysis.

a) Biological Material

*Medicago truncatula* line F83 005.5 plants were cultivated in a controlled environment (16 h/8 h, 20° C./15° C., 60% humidity).

The products studied were applied via the leaves or via the roots.

In the case of application via the leaves, the various solutions of elicitors are sprayed onto the leaves of the 1-month-old plants at the concentration of 1 mg/ml.

In the case of application via the roots, the products are introduced into the nutritive medium.

The study of the overall expression of the genes potentially involved in metabolism and in signaling was pursued by macroarray.

b) Preparation of the Macroarrays

A selection of expressed gene tags (ESTs) of *Medicago truncatula*, based essentially on their involvement in primary metabolism, was carried out using the TGIR and MENS databases.

ESTs belonging to sequences of *Medicago truncatula* [tentative consensus sequences (TCs)] are recovered from the MtBA, MtBB and MtBC libraries.

Two genomic fragments (TC85619, TC85808) are amplified by PCR using the *Medicago truncatula* genomic DNA as primer. These 2 ESTs are then cloned into the pGEM-Teasy vector (Promega) and verified by sequencing.

The other DNA fragments are amplified by PCR using the universal primers complementary to the vector sequences bordering the DNA cloning site. The amplification products are analyzed by electrophoresis and are adjusted to 0.2-0.5 µg/µl with DMSO (50%) and deposited on a membrane by means of a robot (Eurogridder spotting robot).

c) Results

The activity of the ulvans from algae in accordance with Example 1 was studied by simultaneously following the expression of about thirty genes. The various categories of ESTs selected are classified per family: nitrogen metabolism, carbon metabolism and oxidative processes.

The extracts of green algae rich in ulvans bring about the induction of 5 to 7 genes potentially involved in the primary metabolism. Similar responses are obtained for the 2 types of application, i.e. by the leaves and by the roots. The gene induction is greater for the ulvans rich in xyloidurorhamnan acid derivatives, such as, for example, the ulvans of *Ulva armoricana* and of *Enteromorpha intestinalis*. The oligoulvans obtained after hydrolysis show identical results.

TABLE 2C

Effects of the ulvans of various green algae on the expression of certain genes in macroarrays

| | | Ulva | | | | Enteromorpha | |
| --- | --- | --- | --- | --- | --- | --- | --- |
| Gene family | Number of TC[1] | *U. armoricana*[2] Ulvans | Oligoulvans | *U. rigida* | *U. rotundata* | *U. lactuca* | *E. compressa* | *E. intestinalis* |
| Oxidative processes | 8 | 2 | 2 | 2 | 2 | 1 | 2 | 1 |
| Nitrogen metabolism | 6 | 2 | 2 | 1 | 1 | 1 | 1 | 2 |
| Carbon metabolism | 19 | 3 | 3 | 2 | 4 | 3 | 3 | 3 |
| Total | 33 | 7 | 7 | 5 | 7 | 5 | 6 | 6 |

[1] The values correspond to the number of TCs (TIGRs Tentative Consensus Sequences) in each gene family.
[2] The values are means of 3 independent treatments corresponding to the number of genes.

d) Influence of the Number of Treatments on the Sensitization of the Plant

A second series of experiments was carried out in order to evaluate the effect of the sensitization of the plant treated with the extract of *Ulva armoricana*. The effect of a second treatment with the extract of *Ulva armoricana*, 3 days after the first spraying, was thus evaluated. The effects on the gene expression are studied by macroarray.

The treatments carried out in one or two applications induce the expression of a large number of genes involved in the primary and signaling mechanisms. The treatments induce the expression of genes in all the functional categories.

In the case of nitrogen metabolism, a single treatment makes it possible to stimulate the expression of glutamine synthetase and of glutamate dehydrogenase. A double treatment makes it possible to double the number of genes expressed, with, in particular, an overexpression of the genes encoding the ammonium transporter, nitrate reductase, glutamate synthase and glutamine synthetase.

In the case of carbon metabolism, a single treatment makes it possible to stimulate the genes encoding enolase, triose-phosphate isomerase and isocitrate dehydrogenase. A double treatment induces the overexpression of the genes encoding enolase phosphatase and citrate synthase.

In the case of oxidative processes, the induction of the expression of various genes encoding various enzymes: ascorbate peroxidase, peroxidase, superoxide dismutase, gluthatione peroxidase or glutathione S-transferase is observed.

TABLE 2D

Effects of the ulvans of *Ulva armoricana* (AV) on
the expression of certain genes in macroarrays

| | | | Treatment[a] | | | | | |
|---|---|---|---|---|---|---|---|---|
| | | Accession | AV[d] | | | AV + AV[e] | | |
| TC TIGR[b] | Putative function | in GB[c] | 1 | 2 | 3 | 1 | 2 | 3 |
| *Oxidative processes* | | | | | | | | |
| TC76384 | ascorbate peroxidase | AL367369 | 1.60 | 2.40 | 1.00 | 0.90 | 0.74 | NS |
| TC85974 | peroxidase | AL371851 | 1.05 | 1.46 | NS | 2.77 | 5.38 | 2.69 |
| TC76946 | superoxide dismutase | AL375556 | 2.49 | 3.12 | 1.00 | 1.40 | NS | 1.00 |
| TC86106 | glutathione peroxidase | AL374155 | 0.88 | 1.43 | 1.40 | NS | 2.08 | 1.90 |
| TC85451 | glutathione S-transferase | AL368847 | 1.00 | 1.16 | 1.00 | 1.15 | 1.55 | 3.01 |
| TC87485 | similar to a germin | AL373691 | NS | 1.32 | 1.10 | 1.16 | NS | NS |
| *Sugar pathway* | | | | | | | | |
| TC77339 | enolase phosphatase | AL378849 | 1.00 | 0.93 | NS | NS | 1.79 | 2.09 |
| TC85317 | enolase | AL367711 | 1.93 | 1.75 | 1.43 | NS | 0.96 | NS |
| TC85485 | transketolase | AL373090 | 1.00 | 1.00 | 1.00 | 1.00 | NS | 1.00 |
| TC85539 | triosephosphate isomerase | AL365666 | 1.61 | 1.47 | 1.61 | 0.94 | 1.23 | NS |
| TC85625 | isocitrate dehydrogenase | AL368524 | 1.07 | 2.67 | 1.70 | 0.87 | 1.07 | 1.44 |
| TC85966 | citrate synthase | AL374303 | 1.00 | NS | NS | 1.59 | 2.44 | 2.24 |
| *Nitrogen pathway* | | | | | | | | |
| TC76943 | glutamine synthetase | AL366171 | 2.19 | 4.33 | 4.06 | 2.88 | 2.82 | 0.94 |
| TC77277 | nitrite reductase | | 0.84 | NS | 0.83 | 3.56 | 2.20 | 2.34 |
| TC77553 | glutamate synthase | AL366890 | 0.92 | 0.74 | 0.82 | NS | 2.28 | 1.97 |
| TC86604 | glutamate dehydrogenase | AL372216 | 1.00 | 1.51 | 2.21 | 1.00 | NS | NS |
| TC87190 | ammonium transporter | AL370643 | 1.47 | 1.07 | NS | NS | 2.09 | 2.54 |

[a]Values corresponding to the ratios of "intensities of the signals of the plants treated with the extract of *Ulva* (AV)" to the "intensities of the signals of the control plants". Only the genes inducted (ratio >1.5) in at least two independent experiments are included. When we compare the replicats of the three experiments, we can consider that the ratio of a single gene must not be induced in one replicat and repressed in at least one of the others, otherwise it is considered to be not significant (NS).
[b]TC TIGR, number of Tentative Consensus according to The Institute of Genome Research.
[c]GB, accession number in genebank.
[d]AV, a single AV treatment.
[e]AV + AV, two consecutive AV treatments.

EXAMPLE 3

Effects of the Ulvans on Mineral Nitrogen Absorption

The experiment is carried out on wheat. The extract of ulvans is applied to the soil at a rate of 100 and 200 g/ha or to the leaves at a rate of 0.1 and 1 g per liter at the same time as a nitrogenous fertilization (ammonium nitrate).

The cutting of the wheat and the pressing of the bottom ends of the stalks were carried out the same day, at the ear-emergence stage—when the stamens begin to emerge, one week after the application. The quantitative determination of the mineral nitrogen is carried out on the sac liquor.

All the treatments to the leaves or to the soil show a significant effect on mineral nitrogen absorption and confirm the stimulant effect on the genes involved in nitrogen transport, and in particular ammonium transport.

TABLE 3

Effects of the ulvans on mineral nitrogen absorption

| | Ulvan concentration | Mineral nitrogen absorption (as % of the control) |
|---|---|---|
| Soil | 100 g/ha | +12% |
| | 200 g/ha | +24% |
| Via the leaves | 0.1 g/l | +18% |
| | 1 g/l | +32% |

EXAMPLE 4

Effects of the Ulvans on Protein Production

The experiment is carried out on forage pea variety Solara and on maize variety Sabrina. The plants are grown in pots on vermiculite and in a Hoagland's nutritive medium.

The extract of ulvans is incorporated into the nutritive solution before sowing at the dose of 200 g/ha or applied by spraying the leaves at the dose of 1 g per liter. The cultures are carried out for 4 weeks for the pea and 6 weeks for the maize. At this stage, the content and the amount of proteins produced by the root and leaf systems are determined.

In the case of the application via the roots, an increase in the content of root proteins of 16% for the pea and 18% for the maize is observed. The improvement in the root protein content together with the stimulation of the root biomass leads to an increase in the total amount of root proteins produced by each plant: 27% for the pea and 31% for the maize. At the same time, the leaf protein content is increased by 12%, for the 2 cultures.

In the case of the application via the leaves, the increase in protein content is 15% for the pea and 16% for the maize.

TABLE 4

Effects of the ulvans on protein production

| Cultures | Type of application | Root protein content (as % of the control) | Leaf protein content (as % of the control) |
|---|---|---|---|
| Pea | Soil | +16% | +12% |
|  | Leaf spraying | — | +15% |
| Maize | Soil | +18% | +12% |
|  | Leaf spraying | — | +16% |

EXAMPLE 5

Effects of the Ulvans on the Increased Value of the Nitrogen Stores of the Soil and Also on the Effectiveness of Nitrogenous Fertilization The trial is carried out on maize variety Sabrina.

The ulvan derivatives are applied to the soil (200 g/ha) or by leaf spraying (1 g per liter) via the vegetation.

The action of the product is studied, firstly, in an optimal situation (N=180 U) and, secondly, in a disadvantageous situation (absence of nitrogenous fertilization).

The experimental device comprises modes with 4 repetitions.

Each elementary plot consists of 6 rows of 12 m, with harvesting of the 2 central rows. For the plots benefiting from a nitrogenous fertilization, the application is made in the form of urea at the time of tilling (60 U) and at the 8-leaf stage (120 U).

The treatments via the roots and via the leaves are applied approximately 1 month after sowing, at the 5-6-leaf stage.

The verifications carried out on the control and treated batches are performed on yield elements.

TABLE 5

Effects of the ulvans on expression of the yield of maize, grown under nitrogen-limiting conditions

| Nitrogen units/ha | Treatment | Yield at 15% q/ha | Variation/control q/ha | % |
|---|---|---|---|---|
| Dose 0 | Control | 109.45 |  |  |
|  | Ulvans applied to soil | 121.80 | +2.35 | +11% |
|  | Ulvans applied to leaves | 130.57 | +21.12 | +20% |
| Dose 180 | Control | 139.65 |  |  |
|  | Ulvans applied to soil | 144.99 | +5.34 | +4% |
|  | Ulvans applied to leaves | 149.43 | +9.78 | +7% |

The ulvan treatments make it possible to obtain enhanced yields regardless of the mode.

In the case of the application at 180 U, the yield goes from 139.65 q/ha (quintals per hectare) for the control to 144.99 q/ha for the application via the roots, i.e. an increase in yield of more than 5 q/ha.

In the case of the application to the leaves, the gain amounts to more than 9 q/ha, i.e. a 7% increase in yield.

A situation which is more disadvantageous in terms of nitrogen promotes the expression of the ulvan treatments in favor of the yield. The differential then becomes considerable, with a yield which goes from 109.45 q/ha for the control to 121.8 q/ha for the application via the roots, i.e. a gain of 12.35 q/ha. This gain thus corresponds to a yield progression of more than 11%. In the case of the application via the leaves, the gain comes to more than 21.12 q/ha, i.e. a 20% increase in yield.

The ulvan treatments thus make it possible to reduce the depressive effects of a situation which is disadvantageous in terms of nitrogen. The absence of fertilization leads to a drop in yield of 30 q/ha between the controls, whereas it is only 9 q/ha between the treated maize (application via the leaves in the absence of nitrogenous fertilization) and the fertilized control (180 U).

EXAMPLE 6

Effects of the Ulvans on the Reduction of Nitrate Accumulation in the Leaves

A culture of lettuce was realized on vermiculite with the application of a nitrogenous solution leading to the accumulation of nitrates in the leaves.

At the 4-leaf stage, the plantlets are planted out into pots containing vermiculite soaked with a nutritive solution and nitrates (20 meq N/l).

In the case of the treatment via the leaves, the ulvans are sprayed onto the plants 5 days and 10 days after planting out.

In the case of the treatment to the soil, the ulvans are added directly to the nutritive solution.

The analysis of the leaves for nitrates is carried out 20 days after the planting out.

TABLE 6

Effects of the ulvans on the reduction of nitrate accumulation in the leaves

|  | Dose | Reduction of $NO_3^-$ accumulation in the leaf |
|---|---|---|
| Application via the leaves | 0.1 g/l | −12% |
|  | 1 g/l | −34% |
|  | 10 g/l | −36% |
| Application via the soil | 10 g/ha | −6% |
|  | 100 g/ha | −18% |
|  | 1000 g/ha | −20% |

All the treatments with the extract of ulvans result in a reduction in nitrate accumulation in the lettuce leaves. It ranges from 12 to 36% in the case of the treatment via the leaves and from 6 to 20% in the case of the application to the soil.

EXAMPLE 7

Examples of Formulations Incorporating Ulvans

By way of examples, various formulations which can be used according to the invention will be given below, with indications regarding the conditions for using these formulations.

A—Enriching Agents a) CALCAREOUS ENRICHING AGENT

| | |
|---|---|
| Lithothamnium | 1000 kg |
| Ulvan derivatives | QS 200 g/ha |
| Dose applied: 1 T/ha | |
| Calcium carbonate | 1000 kg |
| Ulvan derivatives | QS 1000 g/ha |
| Dose applied: 1 T/ha | | b) ORGANIC ENRICHING AGENT AND CROP SUPPORTS

| | |
|---|---|
| Compost | 500 kg |
| Peat | 500 kg |
| Ulvan derivatives | QS 500 g/ha |
| Dose applied: 1 T/ha | |

B—Root Fertilizers a) NP FERTILIZER

| | |
|---|---|
| Lithothamnium | 310 kg |
| Potassium chloride | 167 kg |
| Urea | 161 kg |
| Aqueous ammonia sulfate | 362 kg |
| Ulvan derivatives | QS 200 g/ha |

| CROPS | DOSE APPLIED (kg/ha) |
|---|---|
| Pasture | 200-400 |
| Cereals | |
| Maize | | b) NPK FERTILIZER + MgO

| | |
|---|---|
| Lithothamnium | 158 kg |
| Aqueous ammonia phosphate | 116 kg |
| Aqueous ammonia sulfate | 186 kg |
| Urea | 156 kg |
| Magnesium oxide | 50 kg |
| Potassium chloride | 334 kg |
| Ulvan derivatives | QS 1000 g/ha |

| CROPS | DOSE APPLIED (kg/ha) |
|---|---|
| Maize | 400-800 |
| Cereals | |
| Grassland | |
| All crops | |

C—Leaf Fertilizers a) Mg SOLUTION

| | |
|---|---|
| Magnesium nitrate | 50 kg |
| Water | 50 kg |
| Ulvan derivatives | QS 1 g/l (final solution applied to the plant) |

| CROPS | Number of applications at various stages of the campaign | Dose per application |
|---|---|---|
| Orchards | 3-6 | 8 l/ha |
| Market garden crops | 2-6 | 5-8 l/ha | b) N Fe Mn SOLUTION

| | |
|---|---|
| Manganese nitrate | 15 kg |
| Ferric chloride | 25 kg |
| Water | 60 kg |
| Ulvan derivatives | QS 0.1 g/l (final solution applied to the plant) |

| CROPS | Number of treatments | Dose per treatment |
|---|---|---|
| Orchards | 4-6 | 3-6 l/ha |
| Market garden crops | 4-6 | 3-6 l/ha | c) N Mn Zn SOLUTION

| | |
|---|---|
| Manganese nitrate | 31 kg |
| Zinc nitrate | 22 kg |
| Water | 47 kg |
| Ulvan derivatives | QS 10 g/l (final solution applied to the plant) |

| CROPS | Number of applications | Dose per application |
|---|---|---|
| Maize | 1-2 | 4-8 l/ha |
| Flax | 1-2 | 4-8 l/ha |
| Beetroot | 1-3 | 4-8 l/ha |
| Soybean | 1-2 | 4-8 l/ha |
| Potato | 1-3 | 4-8 l/ha |
| Pea beans | 2-3 | 4-8 l/ha | d) NPK Trace elements SOLUTION

| | |
|---|---|
| Urea | 17 kg |
| Phosphoric acid | 9 kg |
| Potassium hydroxide | 9 kg |
| Manganese nitrate | 0.7 kg |
| Zinc nitrate | 0.3 kg |
| Copper nitrate | 0.10 kg |
| Ferric chloride | 0.20 kg |
| Boric acid | 0.4 kg |
| Water | 63.3 kg |
| Ulvan derivatives | QS 1 g/l (final solution applied to the plant) |

| CROPS | Number of applicatios | Dose per application |
|---|---|---|
| Market garden crops | 5-10 | 4-6 l/ha |
| Orchards | 4-6 | 4-6 l/ha | e) B P K SOLUTION

| | |
|---|---|
| Potassium hydroxide | 8 kg |
| Phosphoric acid | 1 kg |
| Boric acid | 1 kg |
| Water | 90 kg |
| Ulvan derivatives | QS 10 g/l (final solution applied to the plant) |

| CROPS | Number of applications | Dose per application |
|---|---|---|
| Market garden crops | 2-4 | 3-5 l/ha |
| Fruit crops | 3 | 5 l/ha |

D—Nutritive Solutions for the Roots (Hydroponics, Dropwise)

a) NPK Mg SOLUTION

| | |
|---|---|
| Potassium nitrate | 50 g/l |
| Potassium phosphate | 27 g/l |
| Magnesium sulfate | 49 g/l |
| Ulvan derivatives | 200 g/l (i.e. 1 g/l of final solution applied to the plant) |
| Dilution 1 l per 200 l of water | | b) N Ca Mg SOLUTION

| | |
|---|---|
| Calcium nitrate | 118 g/l |
| Iron chelate | 5 g/l |

-continued

| Ulvan derivatives | 100 g/l (i.e. 0.5 g/l of final solution applied to the plant) |
|---|---|
| Dilution 1 l per 200 l of water | |

The invention claimed is:

1. A method for eliciting nitrogen absorption and protein synthesis in plants, comprising:
administering, to said plants or soils in which said plants are located, an effective amount of (1) ulvans, or (2) a reaction product obtained from the treatment of said ulvans of (1) by chemical hydrolysis or enzymatic hydrolysis, for eliciting nitrogen absorption and protein synthesis in the plants or soils in which the plants are located,
wherein said ulvans of (1) and said reaction product of (2) comprise iduronic acid.

2. The method as claimed in claim 1, wherein the administering is carried out to the plants via the leaves or via the roots.

3. The method as claimed in claim 1, wherein the effective amount administered to the plants is from 0.1 g to 100 g per liter when applied in liquid form via the leaves or in nutritive solution for the roots.

4. A fertilizing product for eliciting nitrogen absorption and protein synthesis in plants, comprising:
an effective amount of at least one member selected from the group consisting of (1) ulvans and (2) a reaction product obtained from the treatment of said ulvan of (1) by chemical hydrolysis or enzymatic hydrolysis, for eliciting nitrogen absorption and protein synthesis in the plants or soils in which the plants are located, in combination with one or more fertilizing substances,
wherein said ulvans of (1) and said reaction product of (2) comprise iduronic acid.

5. The fertilizing product as claimed in claim 4, wherein the fertilizer product is in the form of a liquid and the effective amount is between 0.1 g and 100 g per liter.

6. The method as claimed in claim 1, wherein the effective amount given to the plants or soils is from 10 to 1000 g per hectare when applied in solid form, the solid form being pulverulent or granulated fertilizers.

7. The method as claimed in claim 6, wherein the effective amount given to the plants or soils is about 200 g per hectare.

8. The method as claimed in claim 1, wherein the ulvans are extracted from green algae of the genus *Ulva* or *Enteromorpha*.

9. The method as claimed in claim 1, wherein the ulvans are extracted from at least one selected from the group consisting of the following species of *Ulva* or *Enteromorpha*: *Ulva armoricana, Ulva rigida, Ulva rotundata, Ulva lactuca, Enteromorpha intestinalis* and *Enteromorpha compressa*.

10. The method as claimed in claim 1, wherein the ulvans extracted from algae are obtained by a method including the steps of washing, milling and extracting, wherein extracting involves a solid-liquid separation.

11. The method as claimed in claim 10, wherein the method of obtaining the ulvans extracted from algae further comprises the steps of fractioning, concentrating and dehydrating.

12. The method as claimed in claim 3, wherein the effective amount given to the plants or soils is 1 g per liter.

13. The fertilizing product as claimed in claim 4, wherein the fertilizer product is in the form of a solid, and the effective amount of the at least one member selected from the group consisting of ulvans and a reaction product obtained from the treatment of the ulvans by hydrolysis or enzymatic hydrolysis is between 10 and 1000 g per hectare of treated soil.

14. The fertilizing product as claimed in claim 13, wherein the effective amount given to the plants or soils is 200 g per hectare.

15. The fertilizing product as claimed in claim 13, wherein the solid is powder or granules.

16. The fertilizing product as claimed in claim 4, wherein the ulvans are extracted from green algae of the genus *Ulva* or *Enteromorpha*.

17. The fertilizing product as claimed in claim 4, wherein the ulvans are extracted from at least one selected from the group consisting of the following species of *Ulva* or *Enteromorpha*: *Ulva armoricana, Ulva rigida, Ulva rotundata, Ulva lactuca, Enteromorpha intestinalis* and *Enteromorpha compressa*.

18. The method of claim 1, wherein said ulvans of (1) and said reaction product of (2) comprise a saccharide unit that is derived from iduronic acid.

19. The method of claim 18, wherein the saccharide unit that is derived from iduronic acid is ulvanobiuronic acid 3-sulfate type B, and wherein said ulvans of (1) and said reaction product of (2) further comprise at least one member selected from the group consisting of ulvanobiouronic acid 3-sulfate type A, ulvanobiose acid 3-sulfate and ulvanobiose acid 2',3-disulfate.

20. The fertilizing product as claimed in claim 4, wherein said ulvans of (1) and said reaction product of (2) comprise a saccharide unit that is derived from iduronic acid.

21. The fertilizing product as claimed in claim 20, wherein the saccharide unit that is derived from iduronic acid is ulvanobiuronic acid 3-sulfate type B, and wherein said ulvans of (1) and said reaction product of (2) further comprise at least one member selected from the group consisting of ulvanobiouronic acid 3-sulfate type A, ulvanobiose acid 3-sulfate and ulvanobiose acid 2',3-disulfate.

* * * * *